US008410105B2

(12) United States Patent
Li et al.

(10) Patent No.: US 8,410,105 B2
(45) Date of Patent: Apr. 2, 2013

(54) PYRIDAZINYL AMINE DERIVATIVES, THE USE THEREOF IN THE PREPARATION OF PICORNA VIRUS INHIBITORS

(75) Inventors: Song Li, Beijing (CN); Chunlai Mi, Beijing (CN); Zhibing Zheng, Beijing (CN); Guoming Zhao, Beijing (CN); Xinbo Zhou, Beijing (CN); Zehui Gong, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 17 days.

(21) Appl. No.: 12/946,271

(22) Filed: Nov. 15, 2010

(65) Prior Publication Data

US 2011/0059978 A1  Mar. 10, 2011

Related U.S. Application Data (62) Division of application No. 11/994,166, filed as application No. PCT/CN2005/001913 on Nov. 14, 2005, now Pat. No. 8,076,339.

(30) Foreign Application Priority Data

Jun. 30, 2005  (CN) .......................... 2005 1 0081813

(51) Int. Cl.
*C07D 401/14* (2006.01)
*A61K 31/501* (2006.01)
*A61P 31/12* (2006.01)
*A61P 9/02* (2006.01)
*A61P 1/16* (2006.01)

(52) U.S. Cl. .................................. 514/252.02; 544/238
(58) Field of Classification Search .................. 544/238; 514/252.02
See application file for complete search history.

(56) References Cited

U.S. PATENT DOCUMENTS

| 4,992,433 | A | * | 2/1991 | Stokbroekx et al. ..... 514/217.05 |
| 5,100,893 | A | * | 3/1992 | Stokbroekx et al. ..... 514/252.02 |
| 5,112,825 | A | | 5/1992 | Stokbroekx et al. |
| 5,292,738 | A | | 3/1994 | Stokbroekx et al. |
| 2010/0168120 | A1 | | 7/2010 | Watterson et al. |
| 2011/0021530 | A1 | * | 1/2011 | Billich et al. ................. 514/241 |

FOREIGN PATENT DOCUMENTS

| CN | 1037268 C | 2/1998 |
| EP | 0 398 426 A1 | 11/1990 |
| EP | 0 605 031 A1 | 7/1994 |
| EP | 0 435 381 B1 | 11/1995 |

OTHER PUBLICATIONS

Elinor Simons et al; Frequency, Severity, and Duration of Rhinovirus Infections in Asthmatic and Nonasthmatic Individuals: A Longitudinal Cohort Study, Pediatrics, vol. 112, No. 2, Aug. 2003, 473; http://www.pediatrics.org/cgi/content/full/112/2/S1/473.
Mary Engel; "Rhinovirus strains' genomes decoded; cold cure-all is unlikely", Feb. 13, 2009, downloaded Nov. 13, 2010, http://articles.latimes.com/2009/feb/13/science/sci-cold113.
John S. Tregoning, et al; "Respiratory Viral Infections in Infants; Causes, Clinical Symptoms, Virology, and Immunology", Clinical Microbiology Reviews, Jan. 2010, p. 74-98, vol. 23, No. 1.
Sangita Venkataraman, et al; "Structure of Seneca Valley Virus-001; An Oncolytic Picornavirus Representing a New Genus", Structure, vol. 16, Issue 10, 1555-1561, Oct. 8, 2008.
Britain, pp. 126-127, 2008; http://www.netlibrary.com/nlreader/nlreader.dll?bookid=12783&filename=Page_126.html.
USPTO OA mailed Sep. 20, 2010 in connection with U.S. Appl. No. 11/994,166.
USPTO OA mailed Dec. 3, 2010 in connection with U.S. Appl. No. 11/994,166.
European Search Report: EP 05 81 2984.
USPTO OA mailed Apr. 26, 2011 in connection with U.S. Appl. No. 11/994,166.

* cited by examiner

*Primary Examiner* — Susanna Moore
*Assistant Examiner* — Cecilia M Jaisle
(74) *Attorney, Agent, or Firm* — Ladas & Parry LLP (57) ABSTRACT

The present invention relates to substituted pyridazinylamine derivatives of the formula I or pharmaceutically acceptable salts or hydrates thereof, wherein the substituents are defined as in the description, their preparation process, pharmaceutical compositions comprising them, and uses of the said compounds as picorna virus inhibitors for prevention and/or treatment of diseases caused by picorna viruses.

4 Claims, 2 Drawing Sheets

PYRIDAZINYL AMINE DERIVATIVES, THE USE THEREOF IN THE PREPARATION OF PICORNA VIRUS INHIBITORS

CROSS-REFERENCE TO RELATED ION APPLICATIONS

This application is a divisional of U.S. application Ser. No. 11/994166, filed Feb. 28, 2008 now U.S. Pat. No. 8076339, which claims the benefit of PCT/CN2005/001913, filed on Nov. 14, 2005.

TECHNICAL FIELD

The present invention relates to substituted pyridazinylamine derivatives or pharmaceutically acceptable salts or hydrates thereof, their preparation process, pharmaceutical compositions comprising them, and uses thereof as picorna virus inhibitors in manufacture of medicaments for prevention and/or treatment of diseases caused by picorna virus.

BACKGROUND ART

Picorna viruses are the smallest known animal RNA viruses, they have 7 genera, i.e., rhinovirus genus, enterovirus genus, aphthovirus genus, cardiovirus genus, hepatovirus genus and dual echovirus genus, and other unclassified picorna viruses. Picorna viruses may cause many diseases such as respiratory diseases, hand-foot-mouth diseases, meningitis/encephalitis, poliomyelitis, cardiovascular diseases, hemorrhagic conjunctivitis, hepatitis, etc.

There was a great progression in virology in the later period of 1980s. Several important events in viral life cycle were well described, and many molecular targets had been confirmed. In addition, some novel antiviral drugs appeared during the recent years also promote the rapid development of virology. Picorna virus inhibitors are exactly in increased research stage. The action target of these inhibitors is viral protein 1 (VP1), which has a relatively conservative capsid structure and mediates the adhesion/uncoating process of virus. VP1 from different serotype viruses are highly conservative in structure, but are very important for the replication of viruses. Thus, inhibitors acting on this target are very possible to be drugs against picorna viruses.

SUMMARY OF THE INVENTION

The object of the present invention is to find novel small molecular compounds acting on VP1, which can prevent the adhesion/uncoating of viruses, thereby achieving the purpose of prevention and/or treatment of diseases caused by picorna viruses.

After researches, the inventors of the present invention have found that compounds of the following formula I can act on viral protein 1, thereby blocking the adhesion and uncoating of viruses, so that they can be used for prevention and/or treatment of diseases caused by picorna viruses.

Therefore, the first aspect of the present invention relates to a compound of formula I, or a pharmaceutically acceptable salt or hydrate thereof, wherein:
X is C or N;
Y is O or S,
W is C or N;
$R_1$, $R_2$, $R_3$ each independently is hydrogen or halogen;
$R_4$, $R_5$, $R_6$ each independently is hydrogen, halogen, $C_1$~$C_8$ straight or branched alkyl, $C_1$~$C_8$ straight or branched alkoxy, nitro, cyano, —COOR$_7$, —CH$_2$—O—R$_8$, —CH$_2$COOR$_7$ or —COR$_7$;
Each $R_7$ independently is hydrogen or $C_1$~$C_8$ straight or branched alkyl;
$R_8$ is hydrogen or cyano.

The second aspect of the present invention relates to a process for preparation of the compound of the formula I, or a pharmaceutically acceptable salt or hydrate thereof.

The third aspect of the present invention relates to a pharmaceutical composition comprising at least one of compound of the formula I, or a pharmaceutically acceptable salt or hydrate thereof, and one or more pharmaceutically acceptable carrier or excipient.

The fourth aspect of the present invention relates to a use of the compound of the formula I, or a pharmaceutically acceptable salt or hydrate in manufacture of a medicament for prevention and/or treatment of diseases associated with picorna virus infections.

The fifth aspect of the present invention relates to a method for prevention and/or treatment of diseases associated with picorna virus infections, wherein the said method comprises administrating a preventively and/or therapeutically effective amount of at least one compound of the formula I, or a pharmaceutically acceptable salt or hydrate thereof to such a patient in need thereof.

In one embodiment of the present invention, the present invention relates to a compound of the formula I, or a pharmaceutically acceptable salt or hydrate thereof:

wherein:
X is C or N;
Y is O or S,
W is C or N;
$R_1$, $R_2$, $R_3$ each independently is hydrogen or halogen;
$R_4$, $R_5$, $R_6$ each independently is hydrogen, halogen, $C_1$~$C_8$ straight or branched alkyl, $C_1$~$C_8$ straight or branched alkoxy, nitro, cyano, —COOR$_7$, —CH$_2$—O—R$_8$, —CH$_2$COOR$_7$ or —COR$_7$, each $R_7$ independently is hydrogen or $C_1$~$C_8$ straight or branched alkyl;

$R_8$ is hydrogen or cyano.

According to one preferred embodiment of the present invention, the compound of the formula I is a compound of the formula II, or a pharmaceutically acceptable salt or hydroate thereof:

II wherein:

Y is O or S,

W is C or N;

$R_1$, $R_2$, $R_3$ each independently is hydrogen or halogen;

$R_4$, $R_5$, $R_6$ each independently is hydrogen, halogen, $C_1$~$C_8$ straight or branched alkyl, $C_1$~$C_8$ straight or branched alkoxy, nitro, cyano, —COOR$_7$, —CH$_2$—O—R$_8$, —CH$_2$COOR$_7$ or —COR$_7$, Each $R_7$ independently is hydrogen or $C_1$~$C_8$ straight or branched alkyl;

$R_8$ is hydrogen or cyano.

According to another preferred embodiment of the present invention, the compound of the formula I is a compound of the formula III, or a pharmaceutically acceptable salt or hydrate thereof:

III wherein:

W is C or N;

$R_1$, $R_2$, $R_3$ each independently is hydrogen or halogen;

$R_4$, $R_5$, $R_6$ each independently is hydrogen, halogen, $C_1$~$C_8$ straight or branched alkyl, $C_1$~$C_8$ straight or branched alkoxy, nitro, cyano, —COOR$_7$, —CH$_2$—O—R$_8$, —CH$_2$COOR$_7$, —COR$_7$;

Each $R_7$ independently is hydrogen or $C_1$~$C_8$ straight or branched alkyl;

$R_8$ is hydrogen or cyano.

According to another preferred embodiment of the present invention, the compound of the formula I is a compound of the formula IV, or a pharmaceutically acceptable salt or hydrate thereof:

IV wherein:

$R_1$, $R_2$, $R_3$ each independently is hydrogen or halogen;

$R_4$, $R_5$, $R_6$ each independently is hydrogen, halogen, $C_1$~$C_8$ straight or branched alkyl, $C_1$~$C_8$ straight or branched alkoxy, nitro, cyano, —COOR$_7$, —CH$_2$—O—R$_8$, —CH$_2$COOR$_7$, —COR$_7$;

Each $R_7$ independently is hydrogen or $C_1$~$C_8$ straight or branched alkyl;

$R_8$ is hydrogen or cyano.

According to another preferred embodiment of the present invention, the compound of the formula I is a compound of the formula V, or a pharmaceutically acceptable salt or hydrate thereof:

V wherein:

$R_4$, $R_5$, $R_6$ each independently is hydrogen, halogen, $C_1$~$C_8$ straight or branched alkyl, $C_1$~$C_8$ straight or branched alkoxy, nitro, cyano, —COOR$_7$, —CH$_2$—O—R$_8$, —CH$_2$COOR$_7$ or —COR$_7$;

Each $R_7$ independently is hydrogen or $C_1$~$C_8$ straight or branched alkyl;

$R_8$ is hydrogen or cyano.

According to the present invention, the compound of the formula I of the present invention is selected from the following compounds, or a pharmaceutically acceptable salts or hydrates:

4-{4-[2-(4-butyl-phenoxy)-ethyl]-piperazin-1-yl}-3,6-dichloropyridazine

4-{2-[4-(3,6-dichloropyridazin-4-yl)-piperazin-1-yl]-ethoxy}-phenylacetic acid ethyl ester 3,6-dichloro-4-{4-[2-(2,6-dimethyl-phenoxyethyl)]-piperazin-1-yl}pyridazine 4-{2-[4-(3,6-dichloropyridazin-4-yl)-piperazin-1-yl]-ethoxy}-phenylacetic acid methyl ester 1-(4-{2-[4-(3,6-dichloropyridazin-4-yl)-piperazin-1-yl]-ethoxy}-phenyl)-butan-1-one 4-{2-[4-(3,6-dichloropyridazin-4-yl-piperazin-1-yl)-ethoxy}-benzoic acid methyl ester

1-(4-{2-[4-(3,6-dichloropyridazin-4-yl)-piperazin-1-yl]-ethoxy}-phenyl)-heptan-1-one

4-{2-[4-(3,6-dichloropyridazin-4-yl-piperazin-1-yl)-ethoxy}-benzoic acid propyl ester 4-{2-[4-(3,6-dichloropyridazin-4-yl-piperazin-1-yl)-ethoxy}-phenylacetonitrile 4-{-4-[2-(4-bromo-phenoxy)ethyl]-piperazin-1-yl}-3,6-dichloropyridazine
3,6-dichloro-4-{4-[2-(4-nitro-phenoxy)-ethyl]-piperazin-1-yl}pyridazine
3,6-dichloro-4-{4-[2-(4-methoxy-phenoxy)-ethyl-piperazin-1-yl]}-pyridazine
4-{2-[4-(3,6-dichloropyridazin-4-yl-piperazin-1-yl)-ethoxy}-benzoic acid isopropyl ester
4-{4-[2-(4-butoxy-phenoxy)-ethyl]piperazin-1-yl}-3,6-dichloropyridazine
3,6-dichloro-4-{4-[2-(2-nitro-phenoxy)-ethyl]-piperazin-1-yl}pyridazine
3,6-dichloro-4-[4-(2-p-methylphenoxy-ethyl)-piperazin-1-yl]pyridazine
3,6-dichloro-4-[4-(2-o-methylphenoxy-ethyl)-piperidin-1-yl]-pyridazine
1-(4-{2-[4-(3,6-dichloro-pyridazin-4-yl)-piperazin-1-yl]-ethoxy}-phenyl)-ethanone
3,6-dichloro-4-{4-[2-(2,4-dinitro-phenyl)-ethyl]-piperazin-1-yl}-pyridazine
4-{2-[4-(3,6-dichloropyridazin-4-yl)-piperazin-1-yl]-ethoxy}-benzonitrile
3-{2-[4-(3,6-dichloropyridazin-4-yl)-piperazin-1-yl]-ethoxy}-benzoic acid methyl ester
4-{4-[2-(4-tert-butyl-phenoxy)-ethyl]-piperazin-1-yl}-3,6-dichloro-pyridazine
3,6-dichloro-4-{4-[2-(4-ethoxy-phenoxy)-ethyl]-piperazin-1-yl}-pyridazine
4-{2-[4-(3,6-dichloropyridazin-4-yl)-piperazin-1-yl]-ethoxy}-benzaldehyde
4-{2-[1-(3,6-dichloropyridazin-4-yl)-piperidin-4-yl]-ethoxy}-benzonitrile
1-(4-{2-[1-(3,6-dichloropyridazin-4-yl)-piperidin-4-yl]-ethoxy}-phenyl)-ethanone
3,6-dichloro-4-{4-[2-(4-nitro-phenyl)-ethyl]-piperidin-1-yl}-pyridazine
4-{2-[1-(3,6-dichloropyridazin-4-yl)-piperidin-4-yl]-ethoxy}-benzoic acid methyl ester
4-{2-[1-(3,6-dichloropyridazin-4-yl)-piperidin-4-yl]-ethoxy}-benzoic acid ethyl ester
3,6-dichloro-4-{4-[2-(4-methoxy-phenoxy)-ethyl]piperidin-1-yl}-pyridazine
6-{2-[4-(3,6-dichloropyridazin-4-yl)piperazin-1-yl]-ethoxy}-nicotinic acid ethyl ester; and
6-{2-[4-(3,6-dichloropyridazin-4-yl)piperazin-1-yl]-ethoxy}-nicotinic acid methyl ester.

According to the present invention, the compound of the present invention is prepared according to the following reaction scheme.

A compound of the formula VI reacts with chlorine gas at 100-140° C. in the presence of ferric trichloride as catalyst to form a compound of the formula VII, the compound of the formula VII reacts with a compound of the formula VIII in the presence of sodium carbonate at a temperature ranging from room temperature to 170° C. in chloroform, acetone, dichloromethane, N,N-dimethylformamide, N,N-dimethylacetamide (preferably N,N-dimethylacetamide) as solvent to form a compound of the formula IX, then the compound of the formula IX reacts with a compound of the formula X via a condensation reaction at a temperature ranging from 0° C. to room temperature in an organic solvent such as chloroform, dichloromethane, tetrahydrofuran, etc. (preferably tetrahydrofuran) to obtain a compound of the formula I.

Thus, the process for preparing a compound of the formula I of the present invention comprises the following steps:

(i) Reacting a compound of formula VI with chlorine gas in the presence of ferric trichloride as catalyst to form a compound of the formula VII, wherein, $R_1$, $R_2$, $R_3$ have the same definitions as the above formula I;

wherein, $R_1$, $R_2$, $R_3$ have the same definitions as the above formula I;

(ii) reacting the compound of the formula VII with a compound of the formula VIII to obtain a compound of the formula IX, wherein, X has the same definitions as the above formula I;

wherein, $R_1$, $R_2$, $R_3$ and X have the same definitions as the above formula I;

(iii) reacting the compound of the formula IX with dichlorosulfoxide, then a substituted phenol compound of the formula X via a condensation reaction, wherein, $R_4$, $R_5$, $R_6$, W and Y have the same definitions as the above formula I, to obtain a compound of the formula I, wherein, $R_1$, $R_2$, $R_3$, $R_4$, $R_5$, $R_6$, X, W and Y have the same definitions as the above formula I;

(iv) optionally, the compound of the formula I is converted into a pharmaceutically acceptable salt by treating with a suitable pharmaceutically acceptable acid or base.

According to the present invention, the term "pharmaceutically acceptable salt" used in the present invention includes acid salts formed between the compound of the present invention with a pharmaceutically acceptable inorganic acid or organic acid, or alkali salts formed between the compound of the present invention with a pharmaceutically acceptable base, wherein the acid salts comprise but are not limited to hydrochlorates, hydrobromates, hydriodate, nitrates, sulfates, bisulfates, phosphates, biphosphates, acetates, propionates, butyrates, oxalates, trimethylacetates, adipates, alginates, lactates, citrates, tartrates, succinates, maleates, fumarates, picrates, aspartates, gluconates, benzoates, methanesulfonates, ethanesulfonates, benzenesulfonates, p-methylbenzenesulfonates, and pamoates; and the alkali salts comprises but are not limited to ammonium salts, alkali metal salts such as sodium and potassium salts, alkaline earth metal salts such as calcium and magnesium salts, organic salts such as dicyclohexylamine and N-methyl-D-glucosamine salts, as well as amino acid salts such as arginine and lysine salts.

According to the present invention, the pharmaceutical composition of the present invention comprises an effective amount of a compound of the formula (I) or pharmaceutically acceptable salt or hydrate thereof, and one or more suitable pharmaceutically acceptable carrier or excipient. The pharmaceutically acceptable carriers usable in the pharmaceutical composition of the present invention include but are not limited to ion exchangers, alumina, aluminum stearate, lecithin, serum protein such as human serum protein, buffer substance such as phosphate, glycerol, sorbic acid, potassium sorbate, a mixture of partial glycerides of saturated vegetable fatty acids, water, salts or electrolytes, such as protamine sulfate, disodium hydrogen phosphate, potassium hydrogen phosphate, sodium chloride, zinc salt, colloidal silicon dioxide, magnesium trisilicate, polyvinylpyrrolidone, cellulose substances, polyethyleneglycol, sodium carboxymethyl cellulose, polyacrylate, beeswax, polyethylene-co-polyoxypropylene block polymer, and lanolin.

The compounds of the present invention are a group of strong picorna virus inhibitors, characterized in that they can not only prevent but also treat diseases caused by picorna viruses. The said picorna viruses are rhinoviruses and enteroviruses. The diseases caused by picorna viruses in the present invention include but are not limited to respiratory diseases, hand-foot-mouth diseases, meningitis/encephalitis, poliomyelitis, cardiovascular diseases, hemorrhagic conjunctivitis, hepatitis, etc.

The said respiratory diseases include but are not limited to common colds (summer colds), pharyngitis, tonsillitis, and croup. These diseases usually are caused by rhinoviruses in picorna virus families.

According to the present invention, the pharmaceutical composition of the present invention can be used for administration in any of the following manners: oral administration, atomization inhale, rectal administration, nasal administration, buccal administration, vaginal administration, topical administration, parenteral administration such as subcutaneous, intravenous, intramuscular, intraperitoneal, intrathecal, intraventricular, intrasternal, and intracranial injection or infusion, or administration through explanted reservoir, preferably oral administration, intraperitoneal or intravenous administration. In addition, in order to effectively treat central nervous system disorders with the compound of the present invention, intraventricular administration is preferred for overcoming possible low blood-brain barrier transmission rate.

During oral administration, the compound of the present invention can be processed to form any suitable dosage form for oral administration, which includes but is not limited to tablets, capsules, aqueous solutions, or aqueous suspension; wherein the carriers used for tablets usually include lactose and corn starch, additionally lubricants such as magnesium stearate; the diluents used for capsules usually include lactose and dry corn starch; and for the aqueous suspension, the active components usually are mixed with suitable emulsifying agents and suspending agents. If necessary, the above oral dosage forms may further comprise sweetening agents, flavoring agents or coloring agents.

During rectal administration, the compound of the present invention can be processed to form suppositorium, which is obtained by mixing the drug with a suitable non-irritant excipient, wherein the excipient is in solid form at room temperature, and melts at rectal temperature so as to release the drug. This excipient includes cocoa butter, beeswax, and polyethylene glycol.

During topical administration, especially for the treatment of diseases of afflicted surfaces or organs such as eyes, skins or lower intestinal tract neurogenic diseases, which may be readily reached by topical administration, the compound of the present invention can be formulated into different dosage forms as need for different afflicted surfaces or organs, which are described in detail as follows.

During topical administration at eyes, the compound of the present invention can be formulated to form a micronized suspension or solution, wherein the used carrier is isotonic sterile saline with a certain pH, and a preservative such as chlorobenzyl alkoxide may or may not be added. In addition, as for ophthalmic application, the compound may form an ointment such as Vaseline ointment.

During topical administration on skin, the compound of the present invention can be processed to form appropriate ointments, lotions or creams, wherein the active component is suspended or dissolved in one or more carriers. Herein, the carriers used for ointments include but are not limited to mineral oil, liquid paraffin, white Vaseline, propylene glycol, polyoxyethylene, polyoxypropylene, emulsified wax and water; the carriers used for lotions or creams include but not limited to mineral oil, sorbitan monostearate, Tween 60, cetyl esters wax, hexadecenol, 2-octyldodecanol, benzyl alcohol, and water.

During the topical administration in lower intestinal tract, the compound of the present invention can be processed to form the aforesaid rectal suppository or suitable clysters, and additionally, topical local transdermal patches can also be used.

The compound of the present invention can also be used for administration in form of sterile injections, comprising sterile aqueous injections or oil suspension liquids, or sterile injection solutions, wherein the used carriers and solvents include water, Ringer's solution, and isotonic sodium chloride. In addition, sterilized nonvolatile oil can also be used as solvent or suspending media, such as monoglycerides or diglycerides.

In addition, it should be appreciated that the specific dosage and usage for different patients depend on many factors such as age, body weight, gender, natural health status, nutritional status, active intensity of compound, administration time, metabolic rate, severity of disease, and subjective judgement of doctor during diagnosis and treatment. The preferred dosage is between 0.01-100 mg/kg body weight/day.

SPECIFIC MODELS FOR CARRYING OUT THE INVENTION

The following examples are preferred embodiments for demonstrating the present invention, but are not intend to limit the present invention in any way.

Compound melting points were measured by using RY-1 type melting point detector, wherein the temperature was not corrected. $^1$H NMR was measured by using JNM-ECA-400 nuclear magnetic resonance analyzer (Japan Electronic, Inc.). Mass spectra were measured by using VG-ZabSpec MS analyzer. All solvents used in reactions were pre-treated according standard procedures, unless stated otherwise.

Raw materials used in the reactions, except for 3,6-dichloropyridazine that was purchased from Nanjing Tianzunzezhong Chemical Agents Company, were common agents and were purchased from common suppliers of chemical agents.

EXAMPLE 1

4-{2-[4-(3,6-dichloropyridazin-4-yl)-piperazin-1-yl] ethoxy}-phenylacetic acid methyl ester 1.1. 3,4,6-trichloro-pyridazine To a dry three-necked flask equipped with a refluxing condensor and a ventiduct (connected with a safety flask), 3,6-dichloropyridazine (purchased from Nanjingtianzunzezhong Chemical Agents Company) and anhydrous aluminum trichloride were added, heated by using external heat source to 120° C. to melt reactants, $Cl_2$ gas was fed at this temperature for 3 hours, then the reaction was stopped, cooled to room temperature, trichloromethane was added to dissolve the product, the trichloromethane solution was washed with saturated sodium chloride aqueous solution for twice, the water phase was extracted with trichloromethane for twice, all trichloromethane solutions were combined together and dried over anhydrous sodium sulfate, after trichloromethane was removed by evaporation under vacuum, a reduced pressure distillation was employed to collect fraction of 110-114° C./8 mmHg or 128~9° C./18 mmHg, a white solid was coagulated in a receiving flask. Yield: 55%, m.p. 57~58° C.

1.2. 2-[4-(3,6-dichloropyridazin-4-yl)-piperazin-1-yl]-ethanol

In a 50 mL round bottom flask, 9.18 g (0.05 mol) of 3,4,6-trichloro-pyridazine, 5.30 g (0.05 mol) of anhydrous sodium carbonate and 20 mL of N,N-dimethylacetamide (DMA) were added, stirred at room temperature, then 6.54 g (0.05 mol) of 2-(piperazin-1-yl)-ethanol (dissolved in 10 ml DMA) was added dropwise slowly, stirred overnight, filtered on the next day. 100 mL of distilled water was added into the filter cake and stirred, then filtered again to obtain 10.20 g of a white solid, yield: 73.6%, m.p. 139~141° C. 1H-NMR(400 MHz, CDCl$_3$) δppm: 2.57(br, 1H), 2.66~2.68(t, 2H, J=5.12 Hz), 2.73~2.76(t, 4H, J=4.76 Hz), 3.36~3.38(t, 4H, J=4.52 Hz), 3.68~3.71(t, 2H, J=5.04 Hz), 6.88(s, 1H). 13C-NMR (400 MHz, DMSO-d6) δppm: 155.14, 149.43, 148.70, 116.64, 60.00, 58.49, 52.44, 48.90.

EI-MS m/e: 276.1[M$^+$, 100], 280{[M+4]$^+$, 100}, 245.0, 207.1, 175.1, 100.1, 70.1.

1.3. 4-{2-[4-(3,6-dichloro-pyridazin-4-yl)-piperazin-1-yl]-ethoxy}-phenylacetic acid methyl ester To a 50 mL dry three-necked flask, 1.1085 g (0.004 mol) of a self-made 2-[4-(3,6-dichloro-pyridazin-4-yl)-piperazin-1-yl]-ethanol, 0.54 g (0.003 mol) of p-hydroxybenzoic acid ethyl ester, and 1.224 g of triphenylphosphine, 15 mL of anhydrous tetrahydrofuran was poured into the flask under conditions of ice bath and nitrogen gas protection, then 0.7 mL of diethyl azodiformate (DEAD) dissolved in 5 mL of anhydrous tetrahydrofuran was added dropwise into the flask. After the dropwise addition, the temperature was elevated to room temperature, and the agitation was kept overnight. On the next day, the solvent was removed by using a rotation evaporator, the residue was poured into 100 mL of water, extracted for three times by using 150 mL of dichloromethane, the extract solutions were combined, dried over anhydrous Na$_2$SO$_4$, condensed, and separated by using column chromatograph (eluant, petroleum ether:ethyl acetate:methanol=10:1:0.5) to obtain 0.56 g of 4-{2-[4-(3,6-dichloro-pyridazin-4-yl)-piperazin-1-yl]-ethoxy}-phenylacetic acid methyl ester as a white solid. Yield: 32.9%, m.p. 84 ~86° C. 1H-NMR(400 MHz, DMSO-D6) δppm: 2.64~2.67(m, 4H), 2.75~2.78(t, 2H, J=5.6 Hz), 3.32~3.34(m, 4H), 3.60(s, 5H), 4.08~4.11(t, 2H, J=5.6 Hz), 6.89~6.91(d, 2H, J=8.7 Hz), 7.16~7.18(d, 2H, J=8.7 Hz), 7.40(s, 1H).

EI-MS m/e: 424[M$^+$], 259, 245, 202, 175, 70.0.

According to the same method in 1.3, the following compounds were prepared by using different reactants, i.e., various substituted phenol compounds, to replace the p-hydroxybenzoic acid ethyl ester in 1.3.

EXAMPLE 2

4-{-4-[2-(4-butyl-phenoxy)-ethyl]-piperazin-1-yl}-3,6-dichloropyridazine

This compound was prepared according to the method of 1.3, wherein 4-butylphenol is used instead of phenol used. The titled compound is obtained as a white solid, yield: 35%, m.p. 83~84° C. $^1$H-NMR(400 MHz, CDCl$_3$) δppm: 0.90~0.94(t, 3H, J=7.3 Hz), 1.33~1.37(m, 2H), 1.53~1.58(m, 2H), 2.53~2.57(t, 2H, J=7.8 Hz), 2.78~2.80(t, 4H, J=4.5 Hz), 2.88~2.91(t, 2H, J=5.3 Hz)~3.35 ~3.37(t, 4H, J=4.5 Hz), 4.11~4.14(t, 2H, J=5.3 Hz), 6.85(s, 1H), 6.82~6.84(dd, 2H, J=8.4 Hz), 7.09~7.11(dd, 2H, J=8.7 Hz). EI-MS m/e: 408.0 [M$^+$], 259.0, 245.0, 201.9, 175.0, 70.0.

EXAMPLE 3

4-{2-[4-(3,6-dichloropyridazin-4-yl)-piperazin-1-yl]-ethoxy}-phenylacetic acid ethyl ester This compound was prepared according to the method of 1.3, wherein 4-hydroxybenzoic acid ethyl ester is used instead of phenol used. The titled compound is obtained as a white solid, yield: 32%, m.p. 128~130° C. $^1$H-NMR(400 MHz, DMSO-D$_6$) δ ppm: 1.29~1.32(t, 3H, J=7 Hz), 2.65~2.68(t, 4H, J=4.8 Hz), 2.79~2.82(t, 2H, J=5.6 Hz), 3.32~3.34(t, 4H, J=5 Hz), 4.19~4.22(t, 2H, J=5.6 Hz), 4.25~4.30(q, 2H, J=7.3 Hz), 7.06~7.08(dd, 2H, J=8.7 Hz), 7.89~7.92(dd, 2H, J=8.7 Hz).

EI-MS m/e: 424[M$^+$], 259.0, 245.0, 201.9, 175.0, 70.0.

EXAMPLE 4

3,6-dichloro-4-{4-[2-(2,6-dimethyl-phenoxyethyl)]-piperazin-1-yl}pyridazine

This compound was prepared according to the method of 1.3, wherein 2,6-dimethylphenol is used instead of phenol used. The titled compound is obtained as a white solid, yield: 38.5%, m.p. 94~96° C. $^1$H-NMR(400 MHz, CDCl$_3$): δ ppm: 2.29(s, 6H), 2.83(brs, 4H), 2.90(brs, 2H), 3.41(brs, 4H, J=4.5 Hz), 2.88~2.91(t, 2H, J=5.3 Hz), 3.35~3.37(t, 4H), 3.94(brs, 2H), 6.89(s, 1H), 6.91~6.95(m, 1H), 7.01~7.03(d, 2H, J=7.3 Hz).

EI-MS m/e: 380[M$^+$], 258.9, 247.0, 201.9, 175.0, 91.0, 70.0.

EXAMPLE 5

Compound mc1040720 1-(4-{2-[4-(3,6-dichloropyridazin-4-yl)-piperazin-1-yl]-ethoxy}-phenyl)-butan-1-one This compound was prepared according to the method of 1.3, wherein 1-(4-hydroxy-phenyl)-butan-1-one is used instead of phenol used. The titled compound is obtained as a white solid, yield: 41.5%, m.p. 140~141° C. $^1$H-NMR(400 MHz, CDCl$_3$) δppm: 0.98~1.02(t, 3H, J=7.4 Hz), 1.71~1.79 (m, 2H), 2.80~2.81(m, 4H), 2.88~2.94(m, 4H), 3.36~3.38(m, 4H), 4.20~4.22(t, 2H, J=5.3 Hz), 6.86(s, 1H), 6.93~6.96(dd, 2H, J=8.7 Hz), 7.93~7.96(dd, 2H, J=8.7 Hz).

EI-MS m/e: 422.0[M$^+$], 258.9, 244.9, 201.9, 175.0, 121.0, 70.0.

EXAMPLE 6

4-{2-[4-(3,6-dichloropyridazin-4-yl-piperazin-1-yl)-ethoxy}-benzoic acid methyl ester This compound was prepared according to the method of 1.3, wherein 4-hydroxybenzoic acid methyl ester is used instead of phenol used. The titled compound is obtained as a white solid, yield: 45%, m.p. 138~140° C., $^1$H-NMR(400 MHz, DMSO-D$_6$) δppm: 1.29~1.32(t, 3H, J=7 Hz), 2.65~2.68(t, 4H, J=4.8 Hz), 2.79~2.82(t, 2H, J=5.6 Hz), 3.32~3.34(t, 4H, J=5 Hz), 4.19~4.22(t, 2H, J=5.6 Hz), 4.25~4.30(q, 2H, J=7.3 Hz), 7.06~7.08(dd, 2H, J=9 Hz), 7.40(s, 1H), 7.90~7.92(dd, 2H, J=9 Hz).

EI-MS m/e: 410[M$^+$], 379, 259.0, 247.0, 175.1, 202.0, 92.0, 70.1

EXAMPLE 7

1-(4-{2-[4-(3,6-dichloropyridazin-4-yl)-piperazin-1-yl]ethoxy}-phenyl)-heptan-1-one This compound was prepared according to the method of 1.3, wherein 1-(4-hydroxy-phenyl)-heptan-1-one is used instead of phenol used. The titled compound is obtained as a white solid, yield: 43.5%, m.p. 113~115° C. $^1$HNMR(400 MHz, CDCl$_3$): δppm: 0.87~0.91(t, 3H, J=6.7 Hz), 1.29~1.40

(m, 6H), 1.68~1.76(m, 2H), 2.89~2.93(m, 8H), 3.36~3.38(m, 4H), 4.20~4.22(t, 2H, J=5.32 Hz), 6.86(s, 1H), 6.94~6.96(dd, 2H, J=9 Hz), 7.93~7.96(dd, 2H, J=9 Hz).

EI-MS m/e: 464.0[M$^+$], 258.9, 244.9, 201.8, 175.0, 70.0.

EXAMPLE 8

4-{2-[4-(3,6-dichloropyridazin-4-yl-piperazin-1-yl)-ethoxy]-benzoic acid propyl ester This compound was prepared according to the method of 1.3, wherein 4-hydroxybenzoic acid propyl ester is used instead of phenol used. The titled compound is obtained as a white solid, yield: 47%, m.p. 139~141° C. $^1$H-NMR(400 MHz, DMSO-D$_6$) δppm: 0.94~0.98(t, 3H, J=7.3 Hz), 1.68~1.73(m, 2H), 2.65~2.68(t, 4H, J=4.8 Hz), 2.79~2.82(t, 2H, J=5.6 Hz), 3.33~3.35(t, 4H, J=5 Hz), 4.17~4.22(m, 4H), 7.06~7.08(dd, 2H, J=9 Hz), 7.40(s, 1H), 7.90~7.92(dd, 2H, J=9 Hz).

EI-MS m/e: 438.1[M$^+$], 379, 259.0, 245.0, 175.1, 202.0, 70.1

EXAMPLE 9

4-{2-[4-(3,6-dichloropyridazin-4-yl-piperazin-1-yl)-ethoxy]-phenylacetonitrile

This compound was prepared according to the method of 1.3, wherein 4-hydroxyphenylacetonitrile is used instead of phenol used. The titled compound is obtained as a white solid, yield: 45.5% m.p. 137~139° C., $^1$H-NMR(400 MHz, CDCl$_3$) δppm: 2.78~2.81(t, 4H, J=4.5 Hz), 2.89~2.92(t, 2H, J=5.3 Hz), 3.36~3.38(t, 4H, J=4.8 Hz), 3.70(s, 2H), 4.13~4.16(t, 2H, J=5.3 Hz), 6.86(s, 1H), 6.91~6.93(m, 2H), 7.24~7.26(m, 2H).

EI-MS m/e: 391.0[M$^+$], 259.0, 247.0, 201.9, 175.1, 77.0, 70.0.

EXAMPLE 10

4-{-4-[2-(4-bromo-phenoxy)ethyl]-piperazin-1-yl}-3,6-dichloropyridazine

This compound was prepared according to the method of 1.3, wherein 4-bromophenol is used instead of phenol used. The titled compound is obtained as a white solid, yield: 43%, m.p. 124~126° C. $^1$H-NMR(400 MHz, DMSO-D$_6$) δppm: 2.80(brs, 4H), 2.91(brs, 2H), 3.37(brs, 4H), 4.12(brs, 2H), 6.78~6.82(m, 2H), 6.86(s, 1H), 7.37~7.41(m, 2H).

EI-MS m/e: 431.9[M$^+$], 259.0, 245.0, 201.9, 175.0, 91.0, 70.1.

EXAMPLE 11

3,6-dichloro-4-{4-[2-(4-nitro-phenoxy)-ethyl]-piperazin-1-yl}pyridazine

This compound was prepared according to the method of 1.3, wherein 4-nitrophenol is used instead of phenol used. The titled compound is obtained as a white solid, yield: 41%, m.p. 128~129° C. $^1$H-NMR(400 MHz, DMSO-D$_6$) δppm: 2.66~2.68(m, 4H), 2.81~2.83(t, 2H, J=5.6 Hz), 3.33~3.35(m, 4H), 4.27~4.30(t, 2H, J=5.6 Hz), 7.17~7.20(d, 2H, J=9 Hz), 7.40(s, 1H), 8.20~8.22(d, 2H, J=9 Hz).

EI-MS m/e: 397.0[M$^+$], 259.0, 245.0, 201.9, 175.0, 70.0.

EXAMPLE 12

3,6-dichloro-4-{4-[2-(4-methoxy-phenoxy)-ethyl-piperazin-1-yl]}-pyridazine

This compound was prepared according to the method of 1.3, wherein 4-methoxyphenol is used instead of phenol used. The titled compound is obtained as a white solid, yield: 42.5%, m.p. 138~140° C. $^1$HNMR(400 MHz, CDCl$_3$) δppm: 2.79(brs, 4H), 2.87~2.90(t, 2H, J=5.3 Hz), 3.36~3.38(m, 4H), 3.78(s, 3H), 4.09~4.11(t, 2H, J=5.3 Hz), 6.83~6.89(m, 5H).

EI-MS m/e: 382.1[M$^+$], 259.0, 245.0, 202.0, 175.1, 70.1.

EXAMPLE 13

4-{2-[4-(3,6-dichloropyridazin-4-yl)-piperazin]-1-yl)-ethoxy]-benzoic acid isopropyl ester This compound was prepared according to the method of 1.3, wherein 4-hydroxybenzoic acid isopropyl ester is used instead of phenol used. The titled compound is obtained as a white solid, yield: 52%, m.p. 135~137° C. $^1$H-NMR(400 MHz, DMSO-D$_6$) δppm: 1.29~1.31(d, 6H, J=6.2 Hz) 2.65~2.68(m, 4H), 2.79~2.81(t, 2H, J=5.6 Hz), 3.33~3.34(m, 4H), 4.18~4.21(t, 2H, J=5.6 Hz), 5.06~5.13(m, 1H), 7.05~7.07(dd, 2H, J=9 Hz), 7.40(s, 1H), 7.90~7.92(dd, 2H, J=9 Hz).

EI-MS m/e: 381[M$^+$], 346.0, 258.0, 229.9, 175.9, 124.0, 109.0.

EXAMPLE 14

4-{4-[2-(4-butoxy-phenoxy)-ethyl]-piperazin-1-yl}-3,6-dichloropyridazine

This compound was prepared according to the method of 1.3, wherein 4-butoxyphenol is used instead of phenol used. The titled compound is obtained as a white solid, yield: 40.5%, m.p. 135~136° C. $^1$HNMR(400 MHz, CDCl$_3$) δppm: 0.94~0.99(t, 3H, J=7.7 Hz), 1.47~1.51(m, 2H), 1.73~1.76 (m, 2H), 2.83(brs, 4H), 2.90(brs, 2H), 3.39(brs, 4H), 3.90~3.93(t, 2H, J=6.4 Hz), 4.11~4.12(t, 2H, J=5 Hz), 6.84~6.85(m, 4H), 6.86(s, 1H).

EI-MS m/e: 424.1[M$^+$], 259.0, 245.0, 201.9, 175.1, 110.0, 70.1.

EXAMPLE 15

3,6-dichloro-4-{4-[2-(2-nitro-phenoxy)-ethyl]-piperazin-1-yl}pyridazine

This compound was prepared according to the method of 1.3, wherein 2-nitrophenol is used instead of phenol used. The titled compound is obtained as a white solid, yield: 46.5%, m.p. 125~126° C. $^1$H-NMR(400 MHz, CDCl$_3$) δppm: 2.78~2.81(t, 4H, J=4.5 Hz), 2.89~2.92(t, 2H, J=5.3 Hz), 3.36~3.38(t, 4H, J=4.8 Hz), 3.70(s, 2H), 4.13~4.16(t, 2H, J=5.3 Hz), 6.86(s, 1H), 6.91~6.93(m, 2H), 7.24~7.26(m, 2H).

EI-MS m/e: 391.0[M$^+$], 259.0, 247.0, 201.9, 175.1, 77.0, 70.0.

EXAMPLE 16

3,6-dichloro-4-[4-(2-p-methylphenoxy-ethyl)-piperazin-1-yl]pyridazine

This compound was prepared according to the method of 1.3, wherein 4-methylphenol is used instead of phenol used.

The titled compound is obtained as a white solid, yield: 42%, m.p. 95~96° C. $^1$H-NMR(400 MHz, CDCl$_3$) δppm: 2.23(s, 3H), 2.64~2.66(m, 4H), 2.74~2.77(t, 2H, J=5.7 Hz), 3.32~3.34(m, 4H), 4.05~4.08(t, 2H, J=5.7 Hz), 6.83~6.85 (dd, 2H, J=8.4 Hz), 7.09~7.11(dd, 2H, J=8.4 Hz), 7.40(s, 1H).
EI-MS m/e: 438.2[M$^+$], 379.1, 259.1, 245.1, 175.1, 70.1.

EXAMPLE 17

3,6-dichloro-4-[4-(2-o-methylphenoxy-ethyl)-piperidin-1-yl]-pyridazine

This compound was prepared according to the method of 1.3, wherein 2-methylphenol is used instead of phenol used. The titled compound is obtained as a white solid, yield: 48.5%, m.p. 106~108° C. $^1$H-NMR(400 MHz, DMSO-D$_6$) δppm: 2.13(s, 3H), 2.67~2.69(t, 4H, J=4.5 Hz), 2.79~2.81(t, 2H, J=5.6 Hz), 3.31~3.33(t, 4H, J=4.5 Hz), 4.07~4.10(t, 2H, J=5.6 Hz), 6.80~6.84(m, 1H), 6.89~6.91(d, 1H, J=8.1 Hz), 7.10~7.14(m, 2H), 7.29(s, 1H).
EI-MS m/e: 366.1 [M$^+$], 259.0, 245.0, 202.0, 175.1, 91.0, 70.0.

EXAMPLE 18

1-(4-{2-[4-(3,6-dichloro-pyridazin-4-yl)-piperazin-1-yl]-ethoxy}-phenyl)-ethanone This compound was prepared according to the method of 1.3, wherein 1-(4-hydroxy-phenyl)-ethanone is used instead of phenol used. The titled compound is obtained as a white solid, yield: 47.5%, m.p. 115~117° C. $^1$H-NMR(400 MHz, DMSO-D$_6$) δppm: 2.50~2.52(t, 3H, J=5.6 Hz), 2.65~2.68(m, 4H), 2.79~2.82(t, 2H, J=5.9 Hz), 3.33~3.35(m, 4H), 4.20~4.23(t, 2H, J=5.9 Hz), 7.06~7.08(dd, 2H, J=9 Hz), 7.4 (s, 1H), 7.92~7.94(dd, 2H, J=8.7 Hz).
EI-MS m/e: 394.0[M$^+$], 259.0, 247.0, 201.9, 175.0, 70.0.

EXAMPLE 19

3,6-dichloro-4-{4-[2-(2,4-dinitro-phenyl)-ethyl]-piperazin-1-yl}-pyridazine

This compound was prepared according to the method of 1.3, wherein 2,4-dinitrophenol is used instead of phenol used. The titled compound is obtained as a white solid, yield: 41.5%, m.p. 145~146° C. $^1$H-NMR(400 MHz, CDCl$_3$) δppm: 2.84(brs, 4H), 3.01(brs, 4H), 4.40(brs, 4H), 6.87(s, 1H), 7.23~7.25(d, 1H, J=9.2 Hz), 8.44~8.47(dd, 2H, J$_1$=9.2 Hz, J$_2$=2.8 Hz), 8.77~8.78(d, 1H, J=2.5 Hz).
EI-MS m/e: 443.1[M$^+$], 427.1, 338.3, 245.1, 177.1, 95.1, 83.1, 68.1.

EXAMPLE 20

4-{2-[4-(3,6-dichloro-pyridazin-4-yl)-piperazin-1-yl] ethoxy}-benzonitrile

This compound was prepared according to the method of 1.3, wherein 4-hydroxybenzonitrile is used instead of phenol used. The titled compound is obtained as a white solid, yield: 43.5%, m.p. 175~177° C. $^1$H-NMR(400 MHz, DMSO-D$_6$) δppm: 2.64~2.67(m, 4H), 2.78~2.81(t, 2H, J=5.6 Hz), 3.32~3.35(m, 4H), 4.20~4.23(t, 2H, J=5.6 Hz), 7.13~7.15 (dd, 2H, J=9 Hz), 7.40(s, 1H), 7.76~7.79(dd, 2H, J=9 Hz).
EI-MS m/e: 377[M$^+$], 245, 230, 201.9, 175.1, 119.0, 70.0.

EXAMPLE 21

3-{2-[4-(3,6-dichloropyridazin-4-yl)-piperazin-1-yl] ethoxy}-benzoic acid methyl ester This compound was prepared according to the method of 1.3, wherein 3-hydroxybenzoic acid methyl ester is used instead of phenol used. The titled compound is obtained as a white solid, yield: 52.5%, m.p. 105~107° C. $^1$H-NMR(400 MHz, DMSO-D$_6$) δppm: 2.13(s, 3H), 2.80~2.82(t, 4H, J=4.5 Hz), 2.91~2.94(t, 2H, J=5.3 Hz), 3.36~3.38(t, 4H, J=4.5 Hz), 3.92(s, 3H), 4.18~4.21(t, 2H, J=5.6 Hz), 6.86(s, 1H), 7.11-7.14(m, 1H), 7.34~7.38(t, 1H, J=7.9 Hz), 7.58~7.59(m, 1H), 7.64~7.66(d, 1H, J=7.8 Hz).
EI-MS m/e: 409.9[M$^+$], 378.9, 244.9, 201.9, 175.0, 120.9, 77.0, 70.0.

EXAMPLE 22

4-{-4-[2-(4-tert-butyl-phenoxy)-ethyl]-piperazidin-1-yl}-3,6-dichloropyridazine

This compound was prepared according to the method of 1.3, wherein 4-tert-butyl-phenol is used instead of phenol used. The titled compound is obtained as a white solid, yield: 49%, m.p. 97~99° C. $^1$H-NMR(400 MHz, CDCl$_3$) δppm: 1.30(s, 9H), 2.78~2.80(m, 4H), 2.88~2.91(t, 2H, J=5.6 Hz), 3.35~3.37(m, 4H), 4.12~4.15(t, 2H, J=5.6 Hz), 6.85~6.87 (dd, 2H, J=9 Hz), 6.86(s, 1H), 7.30~7.32(dd, 2H, J=9 Hz).
EI-MS m/e: 408.0[M$^+$], 244.9, 259.0, 175.0, 91.0, 70.0.

EXAMPLE 23

3,6-dichloro-4-{4-[2-(4-ethoxy-phenoxy)-ethyl]-piperazin-1-yl}-pyridazine

This compound was prepared according to the method of 1.3, wherein 4-ethoxyphenol is used instead of phenol used. The titled compound is obtained as a white solid, yield: 54.5%, m.p. 93~95° C. $^1$H-NMR(400 MHz, CDCl$_3$) δppm: 1.38~1.42(t, 3H, J=7 Hz), 3.07(brs, 6H), 3.53(brs, 4H), 3.96~4.01(t, 2H, J=7 Hz), 6.85~6.92(m, 5H).
EI-MS m/e: 396.1[M$^+$], 259.0, 245.0, 202.0, 175.1, 109.0, 70.1.

EXAMPLE 24

4-{2-[4-(3,6-dichloropyridazin-4-yl)-piperazin-1-yl] ethoxy}-benzaldehyde

This compound was prepared according to the method of 1.3, wherein 4-hydroxybenzaldehyde is used instead of phenol used. The titled compound is obtained as a white solid, yield: 52.5%, m.p. 110~112° C. $^1$H-NMR(400 MHz, CDCl$_3$) δppm: 2.81(brs, 4H), 2.95(brs, 2H), 3.38(brs, 4H), 4.24(brs, 2H), 7.02~7.04(dd, 2H, J=8.7 Hz), 7.85~7.87(dd, 2H, J=8.7 Hz), 9.9(s, 1H).
EI-MS m/e: 380.0[M$^+$], 245.0, 229.9, 201.9, 175.0, 70.0.

EXAMPLE 25

4-{2-[1-(3,6-dichloropyridazin-4-yl)-piperidin-4-yl]-ethoxy}-benzonitrile

25.1: 2-[1-(3,6-dichloro-pyridazin-4-yl)-piperidin-4-yl]-ethanol

To a 50 mL round bottom flask, 9.18 g (0.05 mol) of 3,4,6-trichloro-pyridazine, 5.30 g (0.05 mol) of anhydrous sodium carbonate and 20 mL of N,N-dimethylacetamide (DMA) were added, stirred at room temperature, then 6.54 g (0.05 mol) of 2-(piperidin-4-yl)-ethanol (dissolved in 10 mL DMA) was added dropwise slowly, after the dropwise addition, the agitation was kept overnight, the reaction liquid was poured into 100 mL of distilled water on the next day, extracted for three times by using total 200 mL of dichloromethane, the extract solutions were combined together, dried over anhydrous $Na_2SO_4$, concentrated, and separated by using column chromatograph (eluent, petroleum ether:acetone=10:3) to obtain 6 g of 2-[1-(3,6-dichloro-pyridazin-4-yl)-piperidin-4-yl]-ethanol, yield: 43.6%, $^1$H-NMR(400 MHz, DMSO-$D_6$) δppm: 1.21~1.31(m, 2H), 1.39~1.43(m, 2H), 1.59~1.67(m, 1H), 1.76~1.79(dbrs, 2H), 2.82~2.88(dt, 2H, J=11 Hz), 3.45~3.49(m, 2H), 3.70~3.73(dbrs, 2H), 4.40~4.42(t, 1H, J=5 Hz), 7.35(s, 1H).

25.2: 4-{2-[1-(3,6-dichloro-pyridazin-4-yl-)-piperidin-4-yl]-ethoxy}-benzonitrile To a 50 mL dry three-necked flask, 0.554 g (0.002 mol) of self-made 2-[1-(3,6-dichloro-pyridazin-4-yl)-piperidin-4-yl]-ethanol, 0.20 g (0.002 mol) of p-hydroxybenzonitrile, 0.612 g of triphenylphosphine were added, 15 mL of anhydrous tetrahydrofuran was added under conditions of ice bath and nitrogen gas protection, then 0.35 mL of diethyl azodiformate (DEAD) dissolved in 5 mL of anhydrous tetrahydrofuran, was added dropwise into the flask. After the dropwise addition, the temperature was elevated to room temperature, the agitation was kept overnight. On the next day, the solvent was removed by evaporation using a rotation evaporator, the residue was poured into 100 mL of water, extracted for three times by using total 150 mL of dichloromethane, the extract solutions were combined together, dried over anhydrous $Na_2SO_4$, concentrated, and separated by column chromatograph (eluent, petroleum ether:ethyl acetate:methanol=10:3: 0.1) to obtain 0.26 g of 4-{2-[1-(3,6-dichloro-pyridazin-4-yl)-piperidin-4-yl]-ethoxy}-benzonitrile, a white solid. Yield: 34.0%, m.p. 138~139° C. $^1$HNMR(400 MHz, CDCl$_3$) δppm: 1.49~1.55(m, 2H), 1.83~1.86(m, 3H), 1.91~1.94(dbrs, 2H), 2.82~2.87(dt, 2H, J=11.4 Hz), 3.76~3.79(dbrs, 2H), 4.08~4.11(t, 2H, J=5.8 Hz), 6.85(s, 1H), 6.94~6.96(d, 2H, J=8.8 Hz), 7.58~7.61(d, 2H, J=8.8 Hz), 7.40(s, 1H).

EI-MS m/e: 376[M$^+$], 258, 244, 228, 176, 119, 112.

EXAMPLE 26

1-(4-{2-[1-(3,6-dichloropyridazin-4-yl)-piperidin-4-yl]-ethoxy}-phenyl)-ethanone This compound was prepared according to the method of 25.2, wherein 1-(4-hydroxy-phenyl)-ethanone is used instead of phenol used. The titled compound is obtained as a white solid, yield: 42.5%, m.p. 99~100° C. $^1$H-NMR(400 MHz, CDCl$_3$) δppm: 1.49~1.52(m, 2H), 1.84~1.86(m, 3H), 1.92~1.95(m, 2H), 2.57(s, 3H), 2.81~2.88(m, 2H), 3.76~3.79 (m, 2H), 4.11~4.14(t, 2H, J=5.9 Hz), 6.85(s, 1H), 6.92~6.95 (m, 2H), 7.93~7.96(m, 2H). EI-MS m/e: 393.0 [M$^+$], 378.0, 358.0, 258.0, 227.9, 201.9, 175.9, 121.0, 77.0.

EXAMPLE 27

Compound 3,6-dichloro-4-{4-[2-(4-nitro-phenyl)-ethyl]-piperidin-1-yl}-pyridazine This compound was prepared according to the method of 25.2, wherein 4-nitrophenol is used instead of phenol used. The titled compound is obtained as a white solid, yield: 30.5%, m.p. 162~164° C. $^1$H-NMR(400 MHz, CDCl$_3$) δppm: 1.47~1.56(m, 2H), 1.82~1.94(m, 5H), 2.81~2.87(m, 2H), 3.76~3.79(m, 2H), 4.11~4.14(t, 2H, J=5.9 Hz), 6.85(s, 1H), 6.93~6.97(m, 2H), 8.18~8.22(m, 2H).

EI-MS m/e: 396[M$^+$], 258, 228, 244, 176, 109, 67.

EXAMPLE 28

4-{2-[1-(3,6-dichloropyridazin-4-yl)-piperidin-4-yl]-ethoxy}-benzoic acid methyl ester This compound was prepared according to the method of 25.2, wherein 4-hydroxy-benzoic acid methyl ester is used instead of phenol used. The titled compound is obtained as a white solid, yield: 36.5%, m.p. 115~117° C. $^1$H-NMR(400 MHz, DMSO-$D_6$) δppm: 1.32~1.40(m, 2H), 1.75(brs, 3H), 1.83~1.86(d, 2H, J=12.3 Hz), 2.85~2.91(m, 2H), 3.72~3.75 (d, 2H, J=12.3 Hz), 4.12~4.15(t, 2H, J=6.2 Hz), 7.05~7.07 (dd, 2H, J=8.7 Hz), 7.36(s, 1H), 7.90~7.92(dd, 2H, J=8.7 Hz).

EI-MS m/e: 409.0[M$^+$], 374.1, 258.0, 228.0, 175.9, 121.0.

EXAMPLE 29

4-{2-[1-(3,6-dichloropyridazin-4-yl)-piperidin-4-yl]-ethoxy}-benzoic acid ethyl ester This compound was prepared according to the method of 25.2, wherein 4-hydroxybenzoic acid ethyl ester is used instead of phenol used. The titled compound is obtained as a white solid, yield: 26.5%, m.p. 153~155° C. $^1$HNMR(400 MHz, DMSO-$D_6$) δppm: 1.16~1.19(t, 3H, J=7 Hz), 1.23~1.40(m, 3H), 1.75~1.76(brs, 2H), 1.83~1.86(d, 2H, J=12.3 Hz), 2.85~2.91(dt, 2H, J=12.3 Hz), 3.72~3.76(d, 2H, J=12.3 Hz), 4.12~4.15(t, 2H, J=6.2 Hz), 4.24~4.30(q, 2H, J=7 Hz), 7.05~7.07(dd, 2H, J=9 Hz), 7.36(s, 1H), 7.90~7.92 (dd, 2H, J=9 Hz).

EI-MS m/e: 423[M$^+$], 379.0, 351.0, 257.9, 227.9, 175.9, 120.9.

EXAMPLE 30

3,6-dichloro-4-{4-[2-(4-methoxy-phenoxy)-ethyl]-piperidin-1-yl}-pyridazine

This compound was prepared according to the method of 25.2, wherein 4-methoxyphenol is used instead of phenol used. The titled compound is obtained as a white solid, yield: 37.5%, m.p. 119~120° C. $^1$H-NMR(400 MHz, CDCl$_3$) δppm: 1.44~1.53(m, 2H), 1.77~1.82(m, 3H), 1.91~1.94(d, 2H, J=12.3 Hz), 2.81~2.87(m, 2H), 3.75~3.77(d, 2H, J=9.8 Hz), 3.77(s, 3H), 3.98~4.01(t, 2H, J=5.6 Hz), 6.83~6.85(m, 5H).

EI-MS m/e: 381[M$^+$], 346, 258, 229.9, 201.9, 175.9, 124.0, 109.0.

EXAMPLE 31

Compound mc1040709 6-{2-[4-(3,6-dichloro-pyridazin-4-yl)-piperazin-1-yl]-ethoxy}-nicotinic acid ethyl ester

31.1 6-hydroxy-nicotinic acid ethyl ester

To a 100 mL three-necked flask, 0.84 g (0.006 mol) of 6-hydroxynicotinic acid, 30 mL of anhydrous ethanol were added, 3 mL of concentrated sulfuric acid was added dropwise slowly, refluxed overnight, evaporated under vacuum to remove excessive ethanol, the residue was poured into water, extracted with ethyl acetate, washed with saturated sodium hydrogen carbonate, dried with anhydrous sodium sulfate, and concentrated to obtain 0.8 g of 6-hydroxy-nicotinic acid ethyl ester. Yield: 80%.

31.2 6-{2-[4-(3,6-dichloro-pyridazin-4-yl)piperazin-1-yl]-ethoxy}-nicotinic acid ethyl ester To a 50 mL dry three-necked flask, 0.554 g (0.002 mol) of self-made 2-[4-(3,6-dichloro-pyridazin-4-yl)-piperazin-1-yl]-ethanol, 0.28 g (0.002 mol) of 6-hydroxy-nicotinic acid ethyl ester, 0.612 g of triphenylphosphine were added, 15 mL of anhydrous tetrahydrofuran was poured into the flask under condition of ice bath and nitrogen gas protection, then 0.35 mL of diethyl azodiformate (DEAD) dissolved in 5 mL of anhydrous tetrahydrofuran was added dropwise into the flask, after the dropwise addition, the temperature was elevated to room temperature, the agitation was kept overnight. The solvent was removed by evaporation using a rotation evaporator next day, the residue was poured into 100 mL of water, extracted for three times using total 150 mL of dichloromethane, the extract solutions were combined together, dried over anhydrous $Na_2SO_4$, concentrated, and separated by column chromatograph (eluent, petroleum ether:ethyl acetate:methanol=10:5:0.15) to obtain 0.32 g of 4-{2-[4-(3,6-dichloro-pyridazin-4-yl)-piperazin-1-yl]ethoxy}-phenylacetic acid methyl ester, a white solid. Yield: 42.3%, m.p. 140~141° C. $^1$H-NMR(400 MHz, $CDCl_3$) δppm: 1.37~1.41 (t, 3H, J=7.3 Hz), 2.79(brs, 4H), 2.91(brs, 2H), 3.36(brs, 4H), 4.35~4.40(q, 2H, J=7.3 Hz), 4.57(brs, 2H), 6.78~6.80(d, 2H, J=8.7 Hz), 6.86(s, 1H), 8.16~8.18(dd, 1H, $J_1$=8.7 Hz, $J_2$=2.2 Hz).

EI-MS m/e: 425[$M^+$], 258, 244.9, 223, 194.0, 175.0, 82.0, 70.0.

EXAMPLE 32

6-{2-[4-(3,6-dichloropyridazin-4-yl)piperazin-1-yl]-ethoxy}-nicotinic acid methyl ester This compound was prepared according to the method of 31.2, wherein 6-hydroxy-nicotinic acid methyl ester is used instead of phenol used. The titled compound is obtained as a white solid, yield: 36.5%, m.p. 145~146° C. $^1$H-NMR(400 MHz, $CDCl_3$) δppm: 2.65~2.66(m, 4H), 2.77~2.80(t, 2H, J=5.6 Hz), 3.33~3.34(m, 4H), 4.48~4.51(t, 2H, J=5.6 Hz), 6.94~6.96(d, 1H, J=8.7 Hz), 7.38(s, 1H), 8.15~8.18(m, 1H), 8.74~8.75(d, 1H, J=2.2 Hz).

EI-MS m/e: 411.1[$M^+$], 376.1, 258.1, 245.1, 223.1, 202.1, 180.1, 82.1, 70.1.

EXAMPLE 33

Activity Against Picorna Virus of the Compound of the Present Invention in vitro Models Experimental Materials:

HeLa cells (self-preserved in the laboratory)

Rhinovirus-3(HRV-3) (ATCC: VR-1113)

Large ear rabbits (provided by the Center of Laboratory Animals of the Military Medical Science Academy of the PLA)

Preventive Administration:

Principle: the drug and the virus were pre-mixed and incubated to block the procedure of viral uncoating and invasion into cells.

Figure 1:
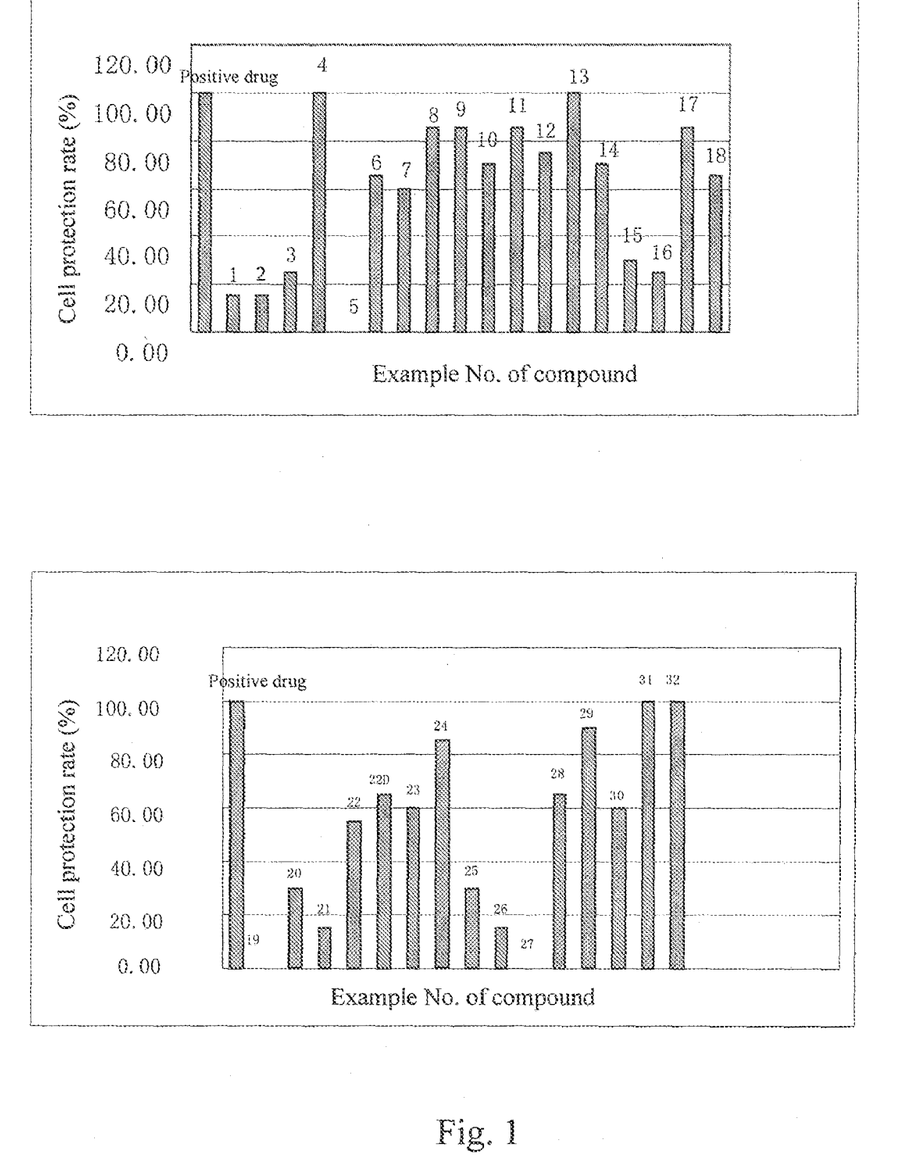
FIG. 1 and FIG. 2 separately show the activity of the compound of the present invention against picorna viruses in vitro models under preventive and therapeutic administration conditions.

Methods: the drug at a concentration of 100 ng/ml was placed into a 12-well plate, then viral dose at $TCID_{50}$ value of about 100 was added, after 0.5 h, 500,000 cells were added into each well, and incubated at 33° C. After three days, when the control group presented 100% cytopathic effect (CPE), the effects of the drug for preventing cells from being phagocytized were observed, and expressed as cell protection rate (%). The results of the preventive administration indicated that different compounds provided various extent of protection effect for cells from being phagocytized; wherein the compounds of Examples 4, 13, 31 and 32 exhibited better effects (see FIG. 1).

Therapeutic Administration:

Purpose: further screening for drugs that exhibited better effects in preventive administration.

Figure 2:
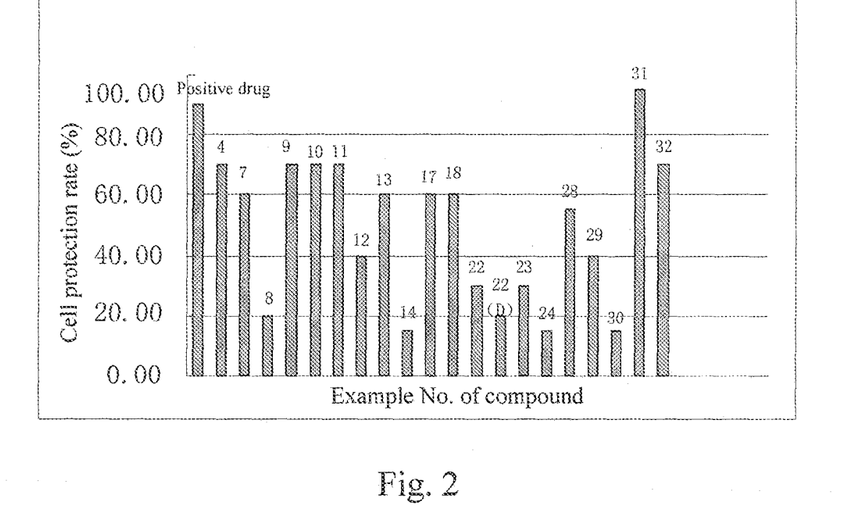

Method: 500,000 cells were added into each well, incubated at 33° C. overnight for adherence, then viral dose at $TCID_{50}$ value of about 100 was added, the culture medium was removed by absorption after 0.5 h, the drug was added into a 12-well plate at a concentration of 100 ng/ml, the total volume of the reaction system was 2 ml. After three days, when the virus control group presented 100% cytophagocytesis (CPE), the effects of the drug for preventing cells from being phagocytized were observed. The results showed that different compounds provided different extents of protection for cells from being phagocytized; wherein the compounds of Example 31 exhibited better effects (see FIG. 2).

Preliminary Results of ex vivo Level Anti-Rhinovirus Drug Screening

Preparation of Tracheal Ring: Rabbits were Executed by Intravenous injection of overdose pentobarbital sodium, then trachea was taken out, tissues and epithelial cells linked to the trachea were peeled off, then the trachea was divided into rings with a width of 6-8 mm.

Method for drug treatment: the tracheal rings were placed in 1640+2% FCS nutritive medium, at the same time, the drug (final concentration: 100 μg/ml) and rhinovirus (final concentration: 106) were added, reacted at 33° C. for 90 min, then reacted at 23° C. for 24 h. 10 μg/ml did not exhibit significant therapeutic effects.

Measurement of constriction and dilatation strength: the tracheal rings were suspended on a triangle support, reached to equilibrium in a 37° C. Havard 20-ml organ bath, exposed to ACh10-7~10-3M, and the maximum constriction or maximum dilatation force under each concentration was recorded, and the results were shown in Table 1 and FIG. 3.

TABLE 1

Ex vivo level experimental data (1) of the compound of Example 31

| Tension (g) | Ach concentration (log M) | | | | | | | | | |
|---|---|---|---|---|---|---|---|---|---|---|
| | −7 | −6 | −5.7 | −5.3 | −5 | −4.7 | −4.3 | −4 | −3.7 | −3 |
| Drug 31 Average | 0.00 | 0.11 | 0.35 | 0.73 | 1.00 | 1.30 | 1.54 | 1.72 | 1.86 | 1.95 |
| Viral Average | 0.00 | 0.11 | 0.53 | 1.06 | 1.66 | 1.92 | 2.32 | 2.62 | 2.87 | 3.05 |
| Control Average | 0.00 | 0.13 | 0.40 | 0.61 | 0.86 | 1.29 | 1.50 | 1.79 | 2.07 | 2.34 |
| SD (Compound of Example 31) | 0.00 | 0.09 | 0.31 | 0.43 | 0.45 | 0.48 | 0.52 | 0.58 | 0.59 | 0.56 |
| SD (virus) | 0.12 | 0.23 | 0.48 | 0.56 | 0.84 | 0.92 | 0.91 | 0.96 | 1.05 | 1.12 |
| SD (control) | 0.06 | 0.21 | 0.37 | 0.54 | 0.63 | 0.57 | 0.63 | 0.55 | 0.56 | 0.65 |

Figure 3:
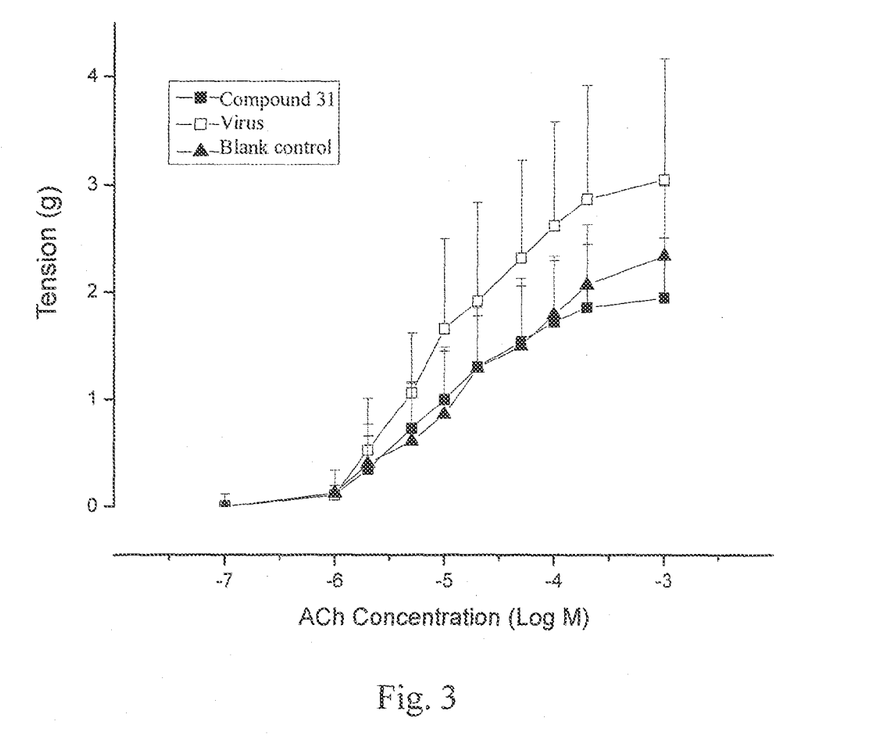
FIG. 3 shows the results of ex vivo anti-rhinovirus level of the compound of Example 31 of the present invention.

As shown in FIG. 3, Ach could cause the increase of smooth muscular tension in a dose-dependent manner, the rhinovirus could enhance the amplitude of increase of tracheal smooth muscular tension induced by Ach, while the compound of Example 31 could obviously inhibit the excessive increase of Ach-induced tracheal smooth muscular tension caused by rhinovirus.

What is claimed is:

1. A compound of formula 1 or a pharmaceutically acceptable salt or hydrate:

I wherein:
X is N;
Y is O or S;
W is N;
$R_1$, $R_2$, and $R_3$ each independently is hydrogen or halogen;
$R_4$, $R_5$, and $R_6$ each independently is hydrogen, halogen, $C_1$-$C_8$ straight or branched alkyl, —$C_1$-$C_8$ straight or branched alkoxy, nitro, cyano, —$COOR_7$, —$CH_2$—O—$R_8$, —$CH_2COOR_7$, or —$COR_7$;
Each $R_7$ independently is hydrogen or $C_1$~$C_8$ straight or branched alkyl; and
$R_8$ is hydrogen or cyano.

2. The compound according to claim 1, having formula III:

III wherein:
W is N;
$R_1$, $R_2$, and $R_3$ each independently is hydrogen or halogen;
$R_4$, $R_5$, and $R_6$ each independently is hydrogen, halogen, $C_1$-$C_8$ straight or branched alkyl, $C_1$-$C_8$ straight or branched alkoxy, nitro, cyano, —$COOR_7$, —$CH_2$—O—$R_8$, —$CH_2COOR_7$, or —$COR_7$;
each $R_7$ independently is hydrogen or $C_1$-$C_8$ straight or branched alkyl; and
$R_8$ is hydrogen or cyano.

3. The compound according to claim 1, wherein said compound is selected from the group consisting of:
6-{2-[4-(3,6-dichloropyridazin-4-yl)piperazin-1-yl]-ethoxy}-nicotinic acid ethyl ester, and
6-{2-[4-(3,6-dichloropyridazin-4-yl)piperazin-1-yl]-ethoxy}-nicotinic acid methyl ester.

4. A pharmaceutical composition, comprising at least one of the compounds of the formula I or a pharmaceutically acceptable salt according to claim 1 as well as one or more pharmaceutically acceptable carriers or excipients.

* * * * *